(12) United States Patent
Nicoletti et al.

(10) Patent No.: US 8,359,904 B2
(45) Date of Patent: Jan. 29, 2013

(54) PHOTOACOUSTIC GAS DETECTOR

(75) Inventors: Sergio Nicoletti, Sinard (FR); Philippe Andreucci, Moirans (FR); Mickaël Brun, Eybens (FR); Serge Gidon, La Murette (FR); Xavier Marcadet, Neuilly sur Seine (FR); Mathieu Carras, Neuilly sur Seine (FR)

(73) Assignees: Commissariat a l'Energie Atomique et aux Energies Albernatives, Paris (FR); Thales, Neuilly sur Seine (FR)

( * ) Notice: Subject to any disclaimer, the term of this patent is extended or adjusted under 35 U.S.C. 154(b) by 293 days.

(21) Appl. No.: 12/909,271

(22) Filed: Oct. 21, 2010

(65) Prior Publication Data
US 2011/0088453 A1 Apr. 21, 2011

(30) Foreign Application Priority Data
Oct. 21, 2009 (FR) ..................................... 09 57377

(51) Int. Cl.
*G01N 21/01* (2006.01)
*G01N 21/61* (2006.01)
*G01N 21/39* (2006.01)
(52) U.S. Cl. ...................................... 73/24.02; 356/437
(58) Field of Classification Search ................. 73/24.02; 356/436, 437
See application file for complete search history.

(56) References Cited

U.S. PATENT DOCUMENTS

| 5,869,749 A | 2/1999 | Bonne |
| 5,933,245 A | 8/1999 | Wood et al. |
| 8,098,376 B2 * | 1/2012 | So et al. ......................... 356/432 |
| 2005/0210956 A1 | 9/2005 | Crane |
| 2008/0159341 A1 * | 7/2008 | Patel et al. ....................... 372/20 |
| 2010/0029026 A1 * | 2/2010 | Berger et al. ..................... 438/24 |
| 2010/0033722 A1 * | 2/2010 | Van Neste et al. ............. 356/432 |
| 2010/0177316 A1 * | 7/2010 | So et al. ......................... 356/432 |
| 2010/0192669 A1 * | 8/2010 | Presura et al. .................. 73/23.3 |
| 2011/0072886 A1 * | 3/2011 | Caneau et al. ................. 73/24.02 |
| 2011/0094291 A1 * | 4/2011 | Gidon et al. .................. 73/24.02 |
| 2011/0102788 A1 * | 5/2011 | Patel et al. ..................... 356/318 |
| 2011/0103411 A1 * | 5/2011 | Patel et al. ....................... 372/19 |
| 2011/0103412 A1 * | 5/2011 | Patel et al. ....................... 372/20 |

(Continued)

FOREIGN PATENT DOCUMENTS

| FR | 2768813 A1 | 3/1999 |
| WO | 2008/030250 A2 | 3/2008 |

OTHER PUBLICATIONS

M. Troccoli, L. Diehl, D. P. Bour, S. W. Corzine, N. Yu, C. Y. Wang, M. A. Belkin, G. Hofler, R. Lewicki, G. Wysocki, F. K. Tittel, F. Capasso., "High-Performance Quantum Cascase Lasers Grown by Metal-Organic Vapor Phase Epitaxy and Their Applications to Trace Gas Sensing," Journal of Lightwave Technology, vol. 26, No. 21, Nov. 1, 2008.*

(Continued)

*Primary Examiner* — Lisa Caputo
*Assistant Examiner* — Punam Roy
(74) *Attorney, Agent, or Firm* — Vedder Price PC

(57) ABSTRACT

A photoacoustic detection device including a nanophotonic circuit including a plurality of semiconductor lasers capable of emitting a different frequencies; input couplers connected to optical waveguides; a multiplexer; an output optical waveguide, emerging into a recess; a tuning fork having its free arms arranged at the output of the output optical waveguide; and means for detecting the vibration of the tuning fork, all these elements being assembled in a monolithic component.

13 Claims, 3 Drawing Sheets

U.S. PATENT DOCUMENTS

| | | | |
|---|---|---|---|
| 2011/0103416 | A1* | 5/2011 | Patel et al. ............... 372/36 |
| 2011/0158270 | A1* | 6/2011 | Patel et al. ............... 372/29.021 |
| 2012/0081708 | A1* | 4/2012 | So et al. ............... 356/432 |
| 2012/0151994 | A1* | 6/2012 | Hung et al. ............... 73/24.02 |
| 2012/0151995 | A1* | 6/2012 | Schade et al. ............... 73/24.02 |

OTHER PUBLICATIONS

S. G. So, A. A. Kosterev, and F. K. Tittel, "Ultra-compact, high efficiency, quartz-enhanced photoacoustic spectroscopy based trace gas sensor platform," IEEE 2006.*

Search Report issued in French Application 09/57377 on Apr. 23, 2010.

"Miniaturization and Integration of Photoacoustic Detection with a Microfabricated Chemical Reactor System", Samara L. Firebaugh, Student Member, IEEE, Klavs F. Jensen, and Martin A. Schmidt, Journal of Microelectromechanical Systems, IEEE Service Center, Piscataway, NJ, vol. 10, No. 2, Jun. 1, 2001, XP011034631, ISSN: 1057-7157.

"Gas-phase Photoacoustic Sensor at 8.41 [mu]m Using Quartz Tuning Forks and Amplitude-Modulated Quantum Cascade Lasers", M.D. Wojcik, M.C. Phillips, B.D. Cannon, and M.S. Taubman, Applied Physcis B, Lasers and Optics, Springer, Berlin, De Lnkd-DOI:10.1007/S00340-006-2394-8, vol. 85, No. 2-3, Aug. 8, 2006, XP019442407, ISSN: 1432-0649.

* cited by examiner

PHOTOACOUSTIC GAS DETECTOR

FIELD OF THE INVENTION

The present invention relates to a photoacoustic type gas detection device.

DISCUSSION OF PRIOR ART

A photoacoustic gas detection device with discrete elements using a tuning fork detector is described in U.S. Pat. No. 7,245,380, FIG. 3 of which is reproduced as appended FIG. 1.

This device comprises a light source (laser) 70 focused by an optical system 71 in an enclosure 60 containing a gas mixture to be analyzed. The pulsed laser beam condensed in the enclosure passes between the arms of a tuning fork 30. The gas mixture is excited differently by specific wavelengths and, when the light is adsorbed, an acoustic emission which excites the tuning fork occurs. The amplitude of the acoustic emission then depends on the light intensity of the laser beam, but also on the concentration of the gas species capable of adsorbing the optical wavelength. Thus, an analysis of the spectral response of a gas sample enables to identify one or several gases constitutive of this sample. A lock-in amplifier 90 enables to lock the laser on the vibration frequency of the tuning fork, whereby the gas vibrates at the natural frequency of the tuning fork. The detection is normally performed by the measurement of a voltage which is generated by piezoelectric effect on the arms of the tuning fork when it starts to vibrate.

This patent discusses the advantages of this type of resonant photoacoustic detection and provides examples of operation at a wavelength close to 1.66 μm. However, such a so-called QEPAS (Quartz Enhanced PhotoAcoustic Spectroscopy) gas detection device made of discrete elements remains limited to laboratory applications. Indeed:
- the materials usable with discrete elements can hardly have transmission wavelengths greater than 2.5 μm while it would be desirable for a gas analysis to operate at wavelengths ranging in a farther infrared, in a range from 3 to 10 μm;
- the device is generally sensitive to temperature variations and to vibrations which may disrupt the alignment;
- the forming of the system, that is, the positioning of its elements and their alignment, must be performed by means of very accurate optical benches, which are difficult to manipulate;
- such a device does not allow to scan a wide range of wavelengths and it is very difficult to replace the laser source.

There thus is a need for photoacoustic gas detection devices overcoming the disadvantages of known devices.

SUMMARY OF THE INVENTION

Thus, an object of an embodiment of the present invention is to provide a photoacoustic detection device having at least some of the following characteristics:
- stability,
- insensitivity to vibrations,
- great accuracy,
- very small dimensions,
- ability to operate at several wavelengths for example ranging from 3 to 10 μm,
- ability to be easily transported and enabling to work during the transport.

An embodiment of the present invention provides a photoacoustic detection device comprising a nanophotonic circuit comprising a plurality of laser diodes capable of emitting at different frequencies; input couplers connected to optical waveguides; a multiplexer; an output optical waveguide having its end provided with focusing means, emerging into a recess; a tuning fork having its free arms arranged at the output of the focusing means of the output optical waveguide; and means for detecting the vibration of the tuning fork, all these elements being assembled in a monolithic component.

According to an embodiment of the present invention, the structure comprising all the lasers is formed in a chip added on a hollowed extension of the support of the nanophotonic circuit.

According to an embodiment of the present invention, the structure comprising all the lasers is directly formed in a multilayer added on the support of the nanophotonic circuit.

According to an embodiment of the present invention, the lasers are of QCL type.

According to an embodiment of the present invention, the cores of the optical waveguides and the arms of the tuning fork are formed from a same material layer.

According to an embodiment of the present invention, the material layer rests on a structure of semiconductor-on-insulator type and, at the level of the waveguides, is coated with a cladding layer of same nature as the upper layer of the structure of semiconductor-on-insulator type and, at the level of the tuning fork arms, is suspended above a recess.

According to an embodiment of the present invention, the upper semiconductor layer of the structure of semiconductor-on-insulator type is a silicon layer, and the cores of the optical waveguides as well as the tuning fork arms are made of germanium.

According to an embodiment of the present invention, the upper surface of the structure of semiconductor-on-insulator type is coated with a silicon nitride layer, the cores of the optical waveguides and the arms of the tuning fork are made of silicon, and the cladding layer also is a silicon nitride layer.

According to an embodiment of the present invention, the device further comprises electronic means for detecting the vibrations of the tuning fork.

According to an embodiment of the present invention, the detection means measure the voltages generated by a piezoelectric effect generated by the material of the tuning fork.

According to an embodiment of the present invention, the detection means comprise electrodes capacitively coupled to the arms of the tuning fork.

The foregoing objects, features, and advantages of the present invention will be discussed in detail in the following non-limiting description of specific embodiments in connection with the accompanying drawings.

DETAILED DESCRIPTION

As usual in the representation of microcomponents, the various dimensions, and especially the layer thicknesses, are not to scale. Those skilled in the art should refer to the current literature on this topic and/or to the specific indications given hereafter as an example.

An embodiment of the present invention provides to form a monolithic photoacoustic detection device. All micro-optical, micro-mechanical and micro-electronic components are made on a same support by using micro- and nanomanufacturing technologies typical in microelectronics and micro-electro-mechanical systems (MEMS). This provides a degree of size control, a structural rigidity, and a robustness which go far beyond what can be obtained with an assembly of discrete elements. The integration of the different components on a same substrate makes it possible to accurately control the general temperature of the detection device by for example using a Peltier-effect cooler. This is particularly important considering the fact that laser sources operating in the average infrared, such as so-called quantum cascade lasers, are generally sensitive to temperature variations which may result in wavelength offsets. Further, forming on a same support an integrated amplifier close to the optical, acoustic, and electronic elements enables to decrease the noise by amplifying low signals in an amplifier integrated in the same device. A considerable gain in terms of signal-to-noise ratio is thus obtained. Finally, the device, due to its miniaturization and to its portability, may be used in circumstances where a device with discrete elements could not be used.

More specifically, the detection device comprises several integrated laser sources which may be selectively activated and directed towards a same waveguide transmitting their beam between the arms of an integrated mechanical resonator. This solves the alignment issues of prior devices.

Figure 1:
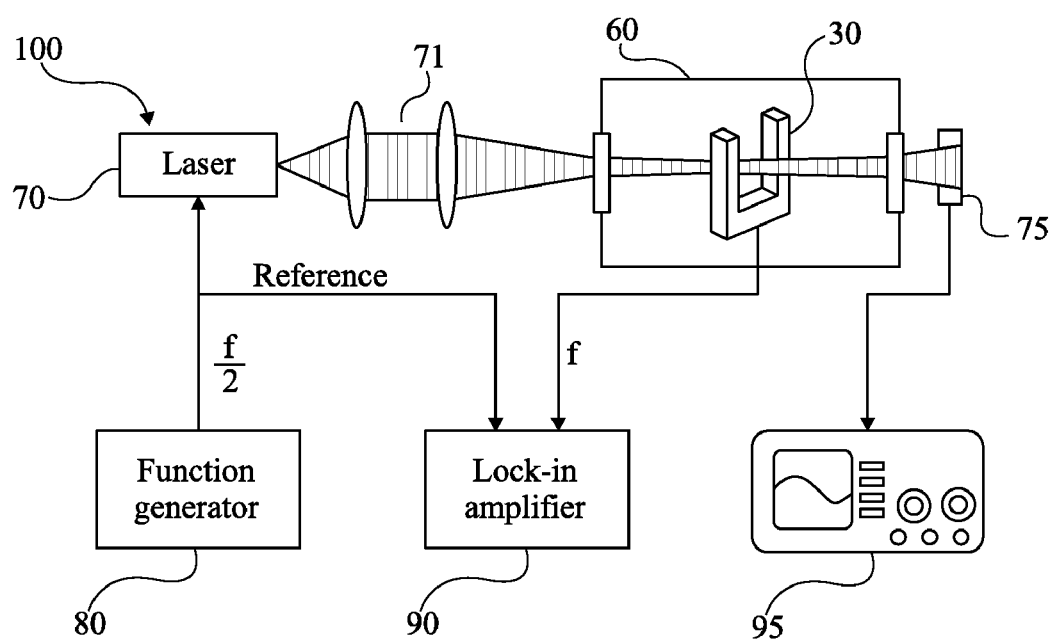
FIG. 1, previously described, corresponds to FIG. 3 of U.S. Pat. No. 7,245,380.
Figure 2A:
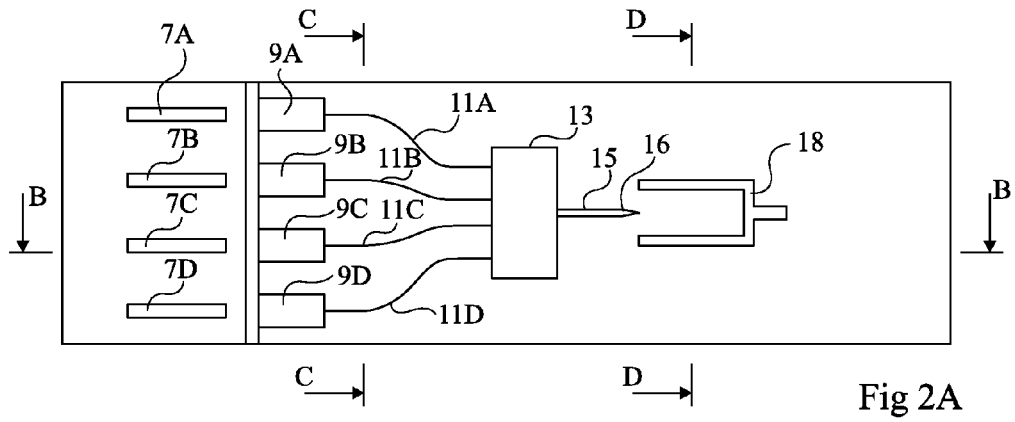
FIG. 2A is a simplified top view of a detection device according to an embodiment of the present invention.
Figure 2B:
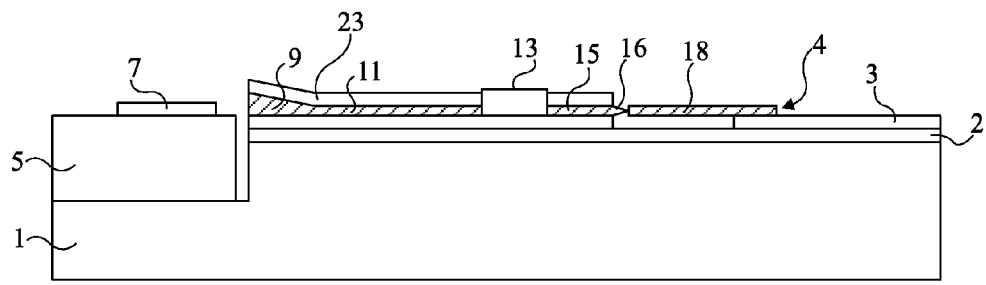
FIG. 2B is a cross-section view along plane BB of FIG. 2A.
Figure 2C:
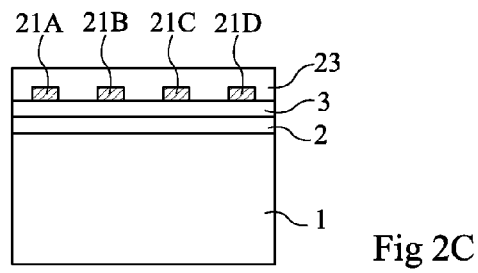
FIG. 2C is a cross-section view along plane CC of FIG. 2A.
Figure 2D:
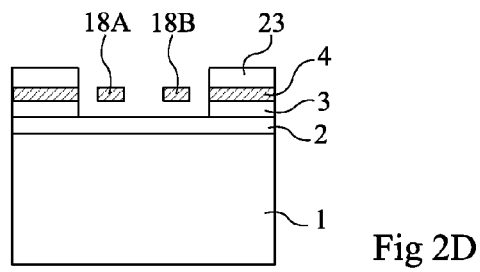
FIG. 2D is a cross-section view along plane DD of FIG. 2A.

FIGS. 2A to 2D respectively show a top view, a cross-section view along plane BB of FIG. 2A, a cross-section view along plane CC of FIG. 2A, and a cross-section view along plane DD of FIG. 2D of an embodiment of a microdetector according to the present invention.

It should be clear that these drawings are extremely simplified and are only intended to ease the understanding of an embodiment of the present invention.

FIGS. 2A to 2D, in which same reference numerals designate same elements, will be generically described.

The structure is entirely formed on a single substrate, for example, a structure of semiconductor on insulator type comprising a support 1, generally a silicon wafer, an insulating layer 2, generally silicon oxide, and a single-crystal semiconductor layer 3, an example of which will be given hereafter.

An element 5 on which are formed semiconductor lasers, preferably of QCL type (Quantum Cascade Laser) is placed on a hollowed part of support 1. As an example, this assembly may be performed according to so-called heterogeneous hybridization techniques currently used in micro- and nanomanufacturing technologies. 4 lasers 7A to 7D, normally set at different frequencies preferably ranging between 3 and 10 μm, have been shown. In practice, a greater number of lasers may be used, for example 6 lasers respectively operating at wavelengths of 4.0, 4.2, 4.4, 4.6, 4.8, 5.0 μm to cover the range from 4 to 5 μm. An advantage of QCL layers is their capacity to be miniaturized and their ability to have their emission wavelength adjusted, that is, each of these lasers may have a wavelength slightly variable around its reference wavelength, where this wavelength adjustment may for example result from the selection of bias currents.

According to an alternative embodiment of the present invention, the material layers necessary to form QCL lasers are directly transferred onto the support, for example, by a molecular bonding method. The QCL lasers will then be directly formed on the final support.

The lasers emit their radiation towards respective couplers 9A to 9D, for example, of tridimensional taper coupler type. These couplers couple the laser beams towards respective optical waveguides 11A to 11D connected to the inputs of an optical multiplexer 13. The multiplexer sends back the incident light of each of input waveguides 11A to 11D to an output waveguide 15. Waveguide 15 preferably comprises a tapered end 16 forming focusing means for concentrating the light into the opening of a tuning fork 18.

According to an advantage of the present invention, components 9 to 18 may be simply formed from a small number of layers of a nanophotonic integrated circuit.

More specifically, the core of waveguides 11 and 15 and the arms of tuning fork 18 are preferably formed from a same layer 4. As more specifically shown in FIG. 2C, each of waveguides 11A to 11D comprises a core, respectively 21A, 21B, 21C, 21D, formed from a layer 4 deposited on semiconductor layer 3 and coated with a cladding layer 23. Similarly, as illustrated in FIG. 2D, arms 18A and 18B of the tuning fork are formed from the same layer 4, a portion of layer 3 being removed under the arms of the tuning fork.

According to an embodiment adapted to an operation in a wavelength range between 3 and 10 μm where the light-gas interaction is maximum but extensible to the far infrared wavelength range (up to 100 μm), layer 3 of the structure of semiconductor-on-insulator type is a silicon layer, the couplers, the cores of the optical waveguide, and the arms of the tuning fork are formed in a germanium layer 4 and the cladding layer also is a silicon layer. Given that the germanium layer and the cladding silicon layer are obtained by growth above a single-crystal semiconductor layer, they may advantageously be single-crystal layers.

According to an alternative embodiment, the cladding layer may be air, the core of each waveguide and the arms of the tuning fork may be made of silicon, the structure being suspended and held by a series of support beams. This embodiment is particularly well adapted to an operation in an extended wavelength range from 3 to 100 μm.

According to another alternative embodiment, the support layer of each waveguide core may be a $Si_3N_4$ layer, the core of each waveguide and the arms of the tuning fork may be made of silicon and the cladding layer may also be made of silicon nitride. This embodiment is particularly well adapted to an operation in a wavelength range from 3 to 6 μm.

The operating mode of this structure will not be described in detail, since as to its principles, it is identical to that of a discrete system, with the advantage of being able to simultaneously operate with several integrated lasers, and to be able to operate over a wide range of wavelengths, given the specific characteristics of the integrated waveguides.

The analysis of the detector vibrations resulting from the creation of acoustic vibrations by the gas receiving the laser beam between the arms of the tuning fork may be carried out in different ways. For example, advantage may be taken from the fact that the arms of the tuning fork are made of a piezoelectric material to directly analyze the signal provided by the piezoelectric elements.

Other analysis means are also possible. For example, to measure the vibration of the arms of the tuning fork, electric conductors may be arranged under the arms of the tuning fork and the signal resulting from the capacitive coupling between the arms of the tuning fork and these electric conductors may be analyzed.

It should be understood that, given the use of an SOI-type structure, the various electronic components intended for the amplification of the signals and their analysis may be formed in the same structure.

Various embodiments with different variations have been described hereabove. It will be within the abilities of those skilled in the art to combine various elements of these various embodiments and variations, without for all this showing any inventive step.

As a variation, instead of being coupled to waveguides 11 by couplers 9, laser 7 may be arranged above these waveguides and be coupled by evanescent waves.

As other variations, the vibration detector may be formed of a simple suspended plate or of an assembly of such plates other than a tuning fork.

FIGS. 3A to 3D are cross-section views illustrating successive steps of an example of a method for manufacturing a detection device according to an embodiment of the present invention.

Figure 3A:
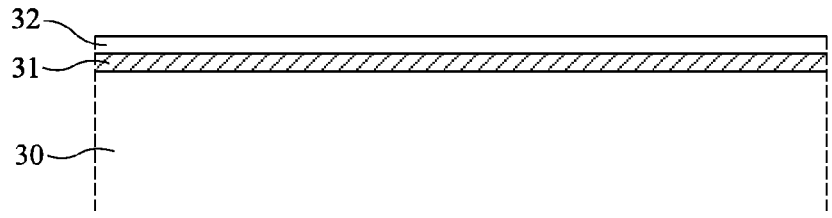
FIGS. 3A to 3D are cross-section views illustrating successive steps of an example of a method for manufacturing a detection device according to an embodiment of the present invention.

FIG. 3A shows a substrate 30 coated with two thin layers 31 and 32. This structure may correspond to a silicon-on-insulator wafer (SOI) where layer 31 generally is a silicon oxide layer and layer 32 generally is a silicon layer. It may however be started from any substrate compatible with a micro- and nanomanufacturing technology. Layer 31 may result from the deposition and/or from an epitaxial growth of a layer having a first optical index $n_{cl}$, typically silicon, but also, for example, $MgF_2$, $CaF_2$, $SrF_2$, $BaF_2$, $PbF_2$, CdF, GaAs, AlGaAs, InP, InAs, InSb, ZnS, CdTe or $Al_2O_3$. Layer 32 may result from any deposition and/or epitaxial growth of a layer having optical index $n_c > n_{cl}$, typically SiGe or Ge but also possibly $MgF_2$, $CaF_2$, $SrF_2$, $BaF_2$, $PbF_2$, CdF, GaAs, AlGaAs, InP, InAs, InSb, ZnS, CdTe or $Al_2O_3$. It should be noted that layer 32 is especially intended to form the core of an optical waveguide and $n_c$ designates the index of this core. Layer 31 is especially intended to form the optical cladding layer of an optical waveguide, which is why its index is designated as $n_{cl}$.

Figure 3B:
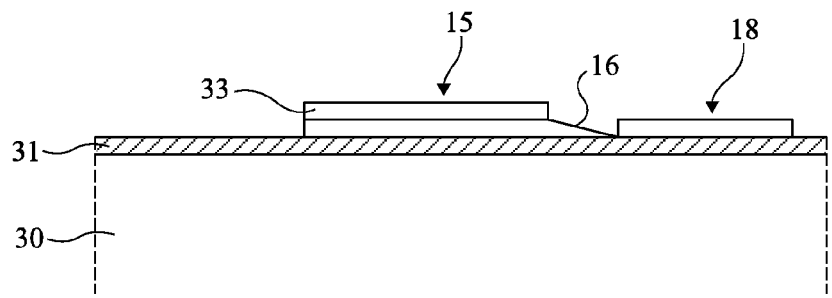

At the step illustrated in FIG. 3B, layer 32 is etched to form photonic components (guide, coupler, multiplexer, focusing device if need be). Advantageously, these patterns are formed by structuration of a simple layer by photolithography and selective etching. The size of the components is selected according to the rules known by those skilled in the art. For example, for the guide, 1.5<V<2 with $$V = \frac{2\pi}{\lambda} \cdot a \cdot nc \cdot \sqrt{\Delta} \quad \text{et} \quad \Delta = \frac{nc^2}{nc^2 - ncl^2} \approx \frac{\Delta n}{n}$$

where a is the half-width of the waveguide. More specifically, FIG. 3B shows a first portion corresponding to tuning fork 18 and a second portion corresponding to waveguide 15. The portion corresponding to waveguide 15 is coated with a second optical cladding layer 33 of index $n_{cl2} < n_c$. Cladding layer 33 will typically be made of silicon and may be made of $MgF_2$, $CaF_2$, $SrF_2$, $BaF_2$, $PbF_2$, CdF, GaAs, AlGaAs, InP, InAs, InSb, ZnS, CdTe or $Al_2O_3$ to define the guide structure. Advantageously, the material of second cladding layer 33 will be the same as that selected for first cladding layer 31.

At the step illustrated in FIG. 3B, tip 16 of the optical waveguide has also been thinned to enhance the concentration of light at the entrance of the tuning fork.

Figure 3C:
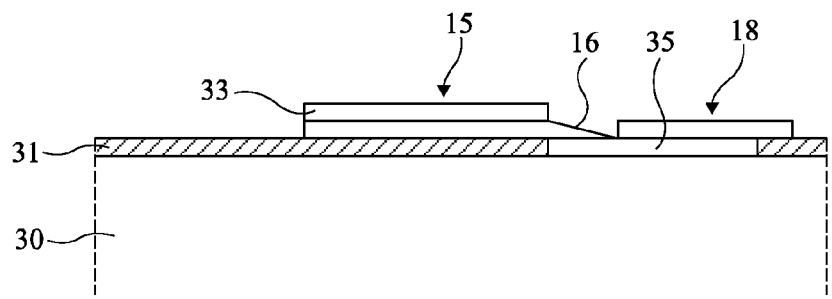

At the step illustrated in FIG. 3C, photoacoustic detector 18 has been completed by forming a recess 35 under the mobile parts of this detector by masking and selective etching of a portion of layer 31.

Figure 3D:
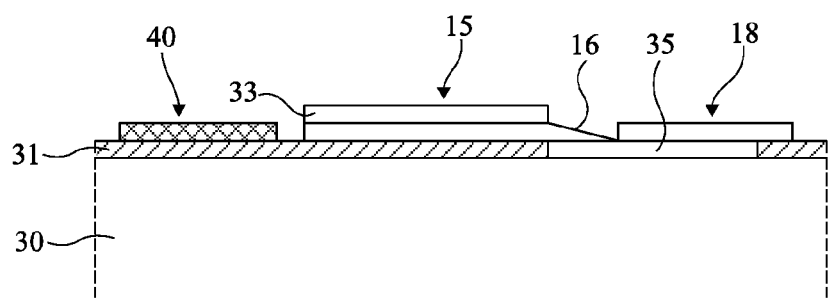

At the next step illustrated in FIG. 3D, a QCL laser 40 is arranged on the left-hand side of the drawing. This laser may be formed by transfer of the multilayer forming the active medium of the QCL by molecular bonding, where the substrate having received the multilayer growth (typically GaAs) is bonded to the main substrate on the multilayer side. The GaAs is then removed. After this, the layer is shaped as for example described in publication Apply Physic Letter 91 (2007) 231101 to form the active QCL laser.

Figure 4:
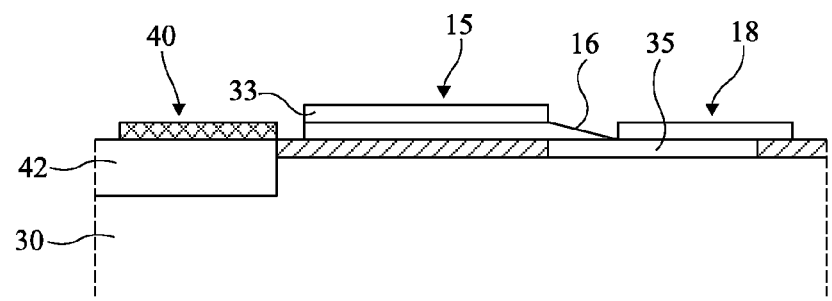
FIG. 4 illustrates a variation of a step of the manufacturing method.

FIG. 4 shows a variation of the embodiment shown in FIG. 3D, corresponding to what has been described in relation with FIG. 2B. In this case, substrate 30 is etched to receive a chip 42 containing the different sources. The lasers are formed on the original substrate, the chip is transferred, aligned and fixed thereon by a ball surface mount or by eutectic bonding, for example, with a gold layer on the substrate and an Sn layer on the chip and a thermal processing to form an Au—Sn alloy.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

The invention claimed is:

1. A photoacoustic detection device comprising a nanophotonic circuit comprising:
   a plurality of laser diodes (7) capable of emitting at different frequencies;
   input couplers (9) connected to optical waveguides;
   a multiplexer (13);
   an output optical waveguide (15), emerging into a recess;
   a tuning fork (18) having its free arms arranged at the level of the output optical waveguide; and
   means for detecting the vibration of the tuning fork,
   all these elements being assembled in a monolithic component.

2. The device of claim 1, wherein the output of the waveguide is provided with focusing means (16).

3. The device of claim 1, wherein the structure comprising all the lasers is formed in a chip added on a hollowed extension of the support of the nanophotonic circuit.

4. The device of claim 1, wherein the structure comprising all the lasers is directly formed in a multilayer added on the support of the nanophotonic circuit.

5. The device of claim 1, wherein the lasers are of QCL type.

6. The device of claim 1, wherein the cores (11) of the optical waveguides and the arms of the tuning fork (18) are formed from a same material layer (4).

7. The device of claim 6, wherein said material layer rests on a structure of semiconductor-on-insulator type and, at the level of the waveguides, is coated with a cladding layer of same nature as the upper layer of the structure of semiconductor-on-insulator type and, at the level of the tuning fork arms, is suspended above a recess.

8. The device of claim 6, wherein the upper semiconductor layer of the structure of semiconductor-on-insulator type is a silicon layer, and the cores of the optical waveguides as well as the tuning fork arms are made of germanium.

9. The device of claim 6, wherein the upper surface of the structure of semiconductor-on-insulator type is coated with a silicon nitride layer, the cores of the optical waveguides and the arms of the tuning fork are made of silicon, and the cladding layer also is a silicon nitride layer.

10. The device of claim 1, further comprising electronic means for detecting the vibrations of the tuning fork.

11. The device of claim 10, wherein the detection means measure the voltages generated by a piezoelectric effect generated by the material of the tuning fork.

12. The device of claim 10, wherein the detection means comprise electrodes capacitively coupled to the arms of the tuning fork.

13. A photoacoustic detection method and device, comprising the steps of:

forming on a substrate (30) a first layer (31) and a second layer (32), the first layer (31) being selected from among the materials comprising Si, $MgF_2$, $CaF_2$, $SrF_2$, $BaF_2$, $PbF_2$, CdF, GaAs, AlGaAs, InP, InAs, InSb, ZnS, CdTe, and $Al_2O_3$, the second layer (32) being selected from among the materials comprising $MgF_2$, $CaF_2$, $SrF_2$, $BaF_2$, $PbF_2$, CdF, GaAs, AlGaAs, InP, InAs, InSb, ZnS, CdTe, and $Al_2O_3$;

etching the second layer to form active photonic components and especially a waveguide element (15) and a tuning fork element (18);

forming an upper cladding layer (33) above the waveguide portion (15), selected from among the materials comprising $MgF_2$, $CaF_2$, $SrF_2$, $BaF_2$, $PbF_2$, CdF, GaAs, AlGaAs, InP, InAs, InSb, ZnS, CdTe, and $Al_2O_3$;

forming a cavity under the tuning fork;

forming QCL lasers and inserting them into the substrate.

* * * * *